United States Patent [19]
Van Tunen et al.

[11] Patent Number: 6,005,167
[45] Date of Patent: Dec. 21, 1999

[54] MALE-STERILE PLANTS, METHOD FOR OBTAINING MALE-STERILE PLANTS AND RECOMBINANT DNA FOR USE THEREIN

[75] Inventors: Adrianus Johannes Van Tunen, Wageningen; Ingrid Maria Van Der Meer, Amsterdam; Josephus Nicolaas Maria Mol, Badhoevedorp, all of Netherlands

[73] Assignee: Mogen International N.V., Leiden, Netherlands

[21] Appl. No.: 08/137,024

[22] PCT Filed: Apr. 15, 1992

[86] PCT No.: PCT/NL92/00075

§ 371 Date: Oct. 14, 1993

§ 102(e) Date: Oct. 14, 1993

[87] PCT Pub. No.: WO92/18625

PCT Pub. Date: Oct. 29, 1992

[30] Foreign Application Priority Data

Apr. 16, 1991 [EP] European Pat. Off. ............. 91200910

[51] Int. Cl.⁶ .............................. A01H 5/00; C12N 15/82
[52] U.S. Cl. ....................... 800/295; 800/260; 800/278; 435/69.1; 536/23.6; 536/419; 536/468
[58] Field of Search ................... 800/205, 255; 435/172.3, 69.1, 240.4, 320.1; 536/23.1, 23.6

[56] References Cited

U.S. PATENT DOCUMENTS

| | | |
|---|---|---|
| 3,710,511 | 1/1973 | Patterson ........................................ 47/58 |
| 5,034,323 | 7/1991 | Jorgensen et al. ..................... 435/172.3 |
| 5,231,020 | 7/1993 | Jorgensen et al. ..................... 435/172.3 |
| 5,283,184 | 2/1994 | Jorgensen et al. ..................... 435/172.3 |
| 5,432,068 | 7/1995 | Albertsen ............................... 435/172.3 |

FOREIGN PATENT DOCUMENTS

| | | |
|---|---|---|
| 0335451 | 4/1989 | European Pat. Off. . |
| 0329308 | 8/1989 | European Pat. Off. . |
| 0335451 | 10/1989 | European Pat. Off. . |
| 8910396 | 11/1989 | WIPO . |
| 9008828 | 8/1990 | WIPO . |
| 9008830 | 8/1990 | WIPO . |
| 9008831 | 8/1990 | WIPO . |

OTHER PUBLICATIONS

Matsuda et al. Plant Cell Physiol. 37(2): 215–222, 1996.
Koltunow, A.M. et al "Different Temporal . . . " The Plant Cell, vol. 21, Americal Society of Plant Physiologists, pp. 1201–1224.
Marrani et al (1990) Nature 347: 737–741.
Finnegan et al (1994) BioTechnology 12 : 883–888.
Van Tunen, A.J., et al. 'Regulation of chalcone flavanone . . . ' in: Plant Molecular Biology., vol. 12, No. 5, 1989, Dordrecht NL, pp. 539–551.
Van Der Meer, I.M., et al. 'Promoter analysis . . . ' in: Plant Molecular Biology., vol. 15, No. 1, 1990, Dordrecht NL, pp. 95–109.
Sun, L.Y., et al. 'Changes in flowering . . . ' in: Plant Science, vol. 80, No. 1–2, 1991, Limerick, Irel. pp. 145–156.
Van Der Meer, I.M., et al. 'Antisense Inhibition . . . ' in: Plant Cell, vol. 4, No. 3, 1992, Rockville US, pp. 253–262.
Taylor, L.P., et al. 'Conditional Male . . . ' in: Journal of Heredity, vol. 83, No. 1, 1992, Washington DC US, pp. 11–17.
Coe, E.H., et al., "White Pollen in Maize" *The Journal of Heredity*, 72:318–320, 1981.
van der Meer, I.M., "Regulation of Flavonoid Gene Expression in Petunia Hybrida: CIS–Acting Elements and Trans–Acting Factors" Free University of Amsterdam, 1991.

*Primary Examiner*—Elizabeth F. McElwain
*Attorney, Agent, or Firm*—Ladas & Parry

[57] ABSTRACT

The present invention provides male-sterile plants. The plants have a recombinant polynucleotide integrated into their genome, essentially comprising an inhibitory gene, which, upon proper expression in the anthers of the plant, is capable of inhibiting expression of one or more genes encoding an enzyme involved in the synthesis of chalcone, or one of its precursors.

33 Claims, 7 Drawing Sheets

```
                    SstI                            PstI
              GAGCTCTAGAGGTGACAGAAATCTGCAG
              CTCGAGATCTCCACTGTCTTTAGACGTC
                   |                                |
CHS-A              TGaTgcTAGAGGTGACAgAAATC
CHS-B         GATGCAATGTTATTAGAGGTGACAAAAATCGACCCAA
CHS-J         GATGCAtgGTTAaT.GAGGaGAaAAAgATtGACCaAA
DFR-A         tATGactTaTccTTAGAGGaGAagtAAtagacgaCAA
```

MALE-STERILE PLANTS, METHOD FOR OBTAINING MALE-STERILE PLANTS AND RECOMBINANT DNA FOR USE THEREIN

FIELD OF THE INVENTION

The invention is related to recombinant DNA, more in particular to recombinant DNA in relation to genetic manipulation of plants. The invention is further related to plants which exhibit nuclear encoded male-sterility, due to expression of the said recombinant DNA, as well as parts of the said plants which are either sexually or asexually reproducible, or both.

BACKGROUND OF THE ART

It has since long been acknowledged that seeds derived through cross-pollination between different varieties of one species, give rise to offspring with better characteristics in terms of yield, environmental fitness, and disease resistance, when compared with the offspring of seeds derived through self-pollination. This effect is generally referred to as the heterosis effect. For this reason, it is an object for the seed industry to obtain hybrid seed in as many agricultural and horticultural crops as possible, because of their higher commercial value.

Unfortunately, however, many crop plants bear the male and female reproductive organs on the same individual, which strongly promotes self-pollination over cross-pollination. Therefore, in order to obtain seeds derived from cross-pollination, it would be desirable to have acceptor plants which are unable to self-pollinate, due to the absence of (properly functioning) pollen. These male-sterile plants or female parents, are then used in cross-fertilization with a male-fertile donor plant to produce hybrid seed.

For the production of hybrid seed on a large scale usually the male-sterile plants and the male-fertile plants are grown together in the field and allowed to cross-pollinate, whereafter the hybrid seed is selected. Depending on the type of male-sterile plants that are used, the selection or separation of hybrid seed is performed before harvesting, i.e. by destroying or removing the male-fertile donor plants which produce non-hybrid seeds, or after harvesting, e.g. on the basis of a marker, such as seed color in maize, or another easily perceptible phenotype. The pre-harvesting selection is possible when the male-fertile parent can be distinguished from the male-sterile parent plant and can subsequently be removed or destroyed. Alternatively, when the male-sterility locus is closely linked to a selectable marker (such as a herbicide resistance), the male-sterile plants, which carry the hybrid seeds, can outcompete the male-fertile plants by applying the appropriate selective pressure.

As male-sterile parental line, use is made of e.g. physically emasculated plants, or if available natural cytoplasmic or nuclear encoded male-sterile mutants. Such naturally male-sterile plants have their disadvantages, be it the very laborious preparation, the presence of additional undesired characteristics, the difficulty of maintenance and propagation, the unpredictable inheritance, or the limited availability of natural male-sterile mutants in commercially interesting crops.

Only recently, genetically engineered nuclear encoded male-sterile plants are known that can be used for the production of hybrid seeds and which lack at least some of the disadvantages of most natural male-sterile mutants.

STATE OF THE ART

The International Patent Application WO 90/08830, ICI proposes methods for the production of restorable male-sterile plants in general terms, essentially comprising expression of a) either a gene encoding a protein inhibitor, or b) a so-called killer gene, wherein said genes are to be expressed in the male flowers, leading to cell death of the anthers and associated tissues. Exemplified killer genes are those which upon expression have an effect on mitochondrial metabolism.

In the International Patent Application WO 90/08831, ICI, the inhibition of cell-respiration by expression of a disrupter gene is disclosed, to inhibit mitochondrial function, eventually resulting in the death of the cells in which these genes are expressed. Preferred disrupter proteins are a) the mammalian uncoupling protein (UCP) b) a mutated form of the gene for the $\beta$-1 subunit of $F_1$-ATPase, such that the changes result in the disability of the subunits to assemble into a functional ATP-synthase (c) a mutated, synthetic form of the oli1 gene encoding subunit 9 of the $F_0$-ATPase, (d) mutated forms of a mitochondrial transit peptide in order to disrupt protein transport to mitochondria (e) gene-constructs involving a fusion between the $\beta$-subunit (ATPase) gene from yeast and the $\beta$-galactosidase gene from *E. coli*, resulting in expression of a disrupting fusion protein. Preferably such expression, according to the specification, should be regulated under the control of a tapetum or pollen-specific promoter.

The International Patent Application WO 89/10396, PGS, proposes methods in general terms for obtaining male-sterile plants, by transforming the nuclear genome of the plant with a so-called male-sterility DNA, which is held to comprise DNA which encodes an RNA, or polypeptide capable of disturbing the proper metabolism, functioning and/or development of any stamen cell in which the male-sterility DNA is expressed, preferably leading thereby to the death of any such stamen cell. Examples of such male-sterility DNA are those encoding DNAses, RNAses, proteases, or enzymes of phytohormone synthesis, such as cytokinin. Alternatively, it is proposed to select male-sterility DNAs from antisense DNAs, 'which encode a strand of DNA complementary to a strand of DNA that is naturally transcribed in the plant's stamen cells'. Apart from the TA29 gene, TA26 gene and the TA13 gene, all tapetum-specific genes derived from tobacco, no clue is given as to what genes are meant. In an article of Koltunow et al., (1990), the clones TA13 and TA29 were identified as encoding so-called Glycine Rich Proteins, whereas clone TA26 corresponded with a cDNA of yet unknown nature.

In the European Patent Application EP-A-0 329 308, Palladin Hybrids, a method to provide male-sterile plants is proposed, comprising producing a genetically transformed female parent, by essentially inserting into the genome of the said plant recombinant DNA sequences comprising antisense DNA which blocks the production of functional pollen grains, or render the developing pollen grains susceptible to a chemical agent or physiological stress which blocks the production of functional pollen grains. Preferably, said antisense genes are expressed under the control of a pollen-specific promoter. Genes which are critical to production of functional pollen grains, according the specification of this Patent Application, are to be selected from genes that are specifically expressed in the microspores, preferably in the premeiotic stage. Examples of microspore specific clones are L4 and L19, derived from *Brassica napus*. Apart from the general indication to premeiotic genes and the expressly mentioned clones, no further teachings are given with respect to the nature of the genes the expression of which is to be blocked.

The EP-A 0 335 451, in the name of the 'Vereniging voor Christelijk Wetenschappelijk Onderwijs', describes that inhibition of expression of a chalcone synthase gene in flowers, using an anti-sense gene construct results in altered flower pigmentation. The anti-sense gene in this experiment was placed under the control of the constitutive cauliflower mosaic virus (CaMV) 35S promoter. Plants with altered flower pigmentation were still capable of producing fertile pollen.

Chalcone synthase is a key-enzyme in the flavonoid biosynthesis. The enzyme catalyzes the stepwise condensation of three acetate residues from malonyl-CoA and one residue of 4-coumaroyl-CoA to yield naringenin chalcone (Heller and Hahlbrock, 1980). Isomerization and further substitution of this central intermediate ultimately leads to the production of flavonoids. Flavonoids are secondary metabolites that are known to have a key-function in the pigmentation of flowers and fruit. In addition, flavonoids appear to be involved in the defense against phytopathogens (Lamb et al., 1989), the protection against UV-light (Schmelzer et al., 1988) and the induction of nodulation (Long et al., 1989). Flavonoids have also been implicated in the regulation of auxin transport (Jacobs and Rubery, 1988) and resistance to insects (Hedin and Waage, 1986).

This multitude of functions of flavonoids requires a proportionally complex regulation of genes encoding different enzymes of the pathway. The expression of, for example, the anthocyanin biosynthesis genes is flower-specific, light-dependent and developmentally regulated (van Tunen et al., 1988; Koes et al., 1989a). However, expression of these genes in other tissues can be induced by UV-light, wounding or fungal attack (Dixon, 1986; Koes et al., 1989a; Lamb et al., 1989).

Comparison of the CHS-A promoter with other promoters from flavonoid synthesis genes that are active in immature anther tissue, e.g. CHS-J, DFR-A and CHI-B revealed the presence of a strongly conserved region, designated as the anther box (van Tunen et al., 1989). Deletion analyses of the CHS-A promoter suggested that the anther box itself is not responsible for anther-specific expression, but may be involved in the regulation of anther-specific expression in conjunction with other sequences present in the CHS-A promoter (van der Meer et al., 1990).

In 1981, Coe et al., (1981), observed that healthy looking white pollen does not function normally in maize, and suggested that pigment synthesis or deposition may be vital to pollen function. However, in the article the involvement of flavonoids in pollen development was not concluded, if not called in doubt. As far as we know, in the years thereafter no conclusive evidence has been reported, regarding a function of flavonoids in the development of viable pollen.

DEFINITIONS

Figure 1:
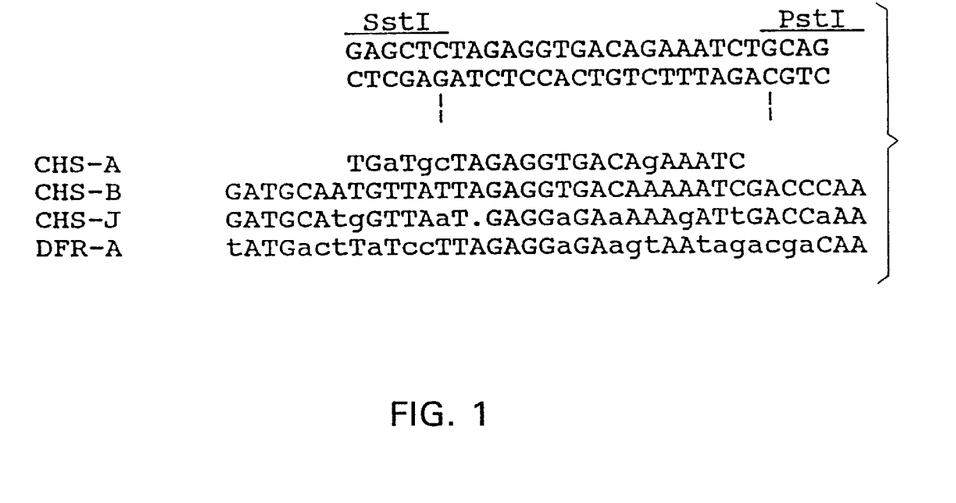
FIG. 1 shows the sequence of a synthetic anther box of CHS-A, which was inserted into the CaMV 35S promoter. Beneath it the anther boxes derived from different flavonoid biosynthesis genes are presented. Numbers between parentheses indicate the relative position of the anther box with respect to the transcription start site of the gene of origin.

Antherbox: a nucleotide sequence which is identical or at least very homologous to any of the sequences depicted in FIG. 1.

Antisense gene: a gene, or a nucleotide sequence derived thereof, having a homology of more than 50%, preferably more than 80% with a target gene as defined herein, and which is linked to a promoter in the inverse 5' to 3' orientation with respect to the target gene.

Gene: a nucleotide sequence that can be expressed in the form of an RNA molecule and/or a polypeptide.

Hybrid promoter: a promoter which is composed of nucleotide sequences, or single nucleotides, which are naturally not associated with each other, or naturally not in that order.

Inhibitory gene: a gene or antisense gene, expression of which ultimately leads to inhibition of expression of a target gene as defined herein.

Promoter: a nucleotide sequence which is capable of promoting expression of a gene or antisense gene, or nucleotide sequences derived thereof, said expression being in the form of an RNA molecule and/or a polypeptide.

Restoration gene: a gene, preferably a fusion gene, comprising at least a nucleotide sequence that is sufficiently identical, similar or homologous to part of a target gene as herein defined to be capable, upon expression, of complementary association with a transcript produced by an inhibitory gene as herein defined.

Target gene: a gene, expression of which is to be inhibited by proper expression of a suitable inhibitory gene as herein defined.

For the purpose of this application, all indications of numerical base positions are relative to the putative transcription start site of the corresponding gene under its control.

SUMMARY OF THE INVENTION

It is an object of the present invention to provide plants which are male-sterile and which can be safely used for the production of hybrid seed. Moreover it is an additional object to provide male-sterile plants, which can be obtained in homozygous form to cost-effectively produce heterozygous male-sterile plants on a large scale.

The present invention provides recombinant polynucleotides which can be suitably used for obtaining a male-sterile plant, essentially comprising:

(a) an inhibitory gene capable of inhibiting expression of a target gene in the said plant encoding an enzyme of the chalcone biosynthesis pathway, and (b) a promoter that is active in anthers of said plant, operably linked to said inhibitory gene as to achieve expression thereof in the anthers of said plant.

A preferred target gene according to the invention encodes an enzyme selected from the group consisting of cinnamate 4-hydroxylase (C4H; E.C. 1.14.13.11), 4-coumaroyl-CoA ligase (4CL; E.C. 6.2.1.12), and chalcone synthase (CHS; E.C. 2.3.1.74.). Especially preferred as target gene is the gene encoding chalcone synthase (CHS) in the plant.

In a preferred embodiment of the invention the inhibitory gene is an antisense gene directed against the target gene.

In another preferred embodiment according to the invention the promoter that is active in the anthers of a plant comprises a fragment of a high-level promoter and an anther box obtainable from the promoter region of a group of genes consisting of the chs-A gene, the chi-B gene, the chs-J gene, and the dfrA gene from Petunia. In particularly preferred embodiment the high-level promoter comprises a fragment of the CaMV 35S promoter and an anther box having the sequence:

TAGAGGTGACAGAAAT (SEQIDNO: 2)

inserted in said fragment at position −90 with respect to the transcription start site.

The invention also provides a method for obtaining a male-sterile plant, comprising the steps of (a) transferring a recombinant polynucleotide according to the invention to cells of a male-fertile plant, (b) generating whole new plants from cells having incorporated said recombinant polynucleotide, and (c) selecting a plant that is male-sterile.

Yet another embodiment of the invention is a recombinant plant genome, comprising incorporated therein a recombinant polynucleotide according to the invention.

Another embodiment of the invention comprises a nucleotide sequence having the sequence:

TNGAGGWGAMRDARWW (SEQIDNO: 1), wherein N=A, G, C, or T; W=A or T; M=A or C; R=A or G and D=A, G, or T for use in a method for obtaining a male-sterile plant. A still more preferred embodiment of the invention comprises an oligonucleotide sequence having a sequence selected from the group consisting of:

| (a) | TAGAGGTGACAGAAAT (SEQIDNO: 2) |
|---|---|
| (b) | TAGAGGTGACAAAAAT (SEQIDNO: 3) |
| (c) | TNGAGGTGACAAAGAT (SEQIDNO: 4) |
| (d) | TAGAGGAGAAGTAATA (SEQIDNO: 5) | wherein N=A, G, C, or T, for use in a method for obtaining a male-sterile plant.

The invention also provides a method for obtaining self-fertilized seed of a male-sterile plant having incorporated a recombinant polynucleotide according to the invention, comprising the steps of:

(a) contacting the pistil of a male-sterile plant with pollen of the same male-sterile plant in the presence of a suitable flavonoid compound, and (b) allowing the pollen to germinate on the pistil and fertilise the male-sterile plant, and (c) allow the plant to set seed.

Especially preferred in the above method is a flavonoid compound selected from the group consisting of myricetin, quercetin and kaempferol, preferably within a concentration range of 100 nm to 3 $\mu$M.

In a yet further preferred embodiment of the invention a method is provided for a cost effective production of hybrid seed, due to use of large numbers of heterozygous male-sterile plants, which have been obtained by crossing a homozygous male-sterile plant of the desired variety with a male-fertile plant of the same variety.

The invention further encompasses (hybrid) seed obtained through crossing or selfing of any of the plants according to the invention.

Other preferred embodiments of the invention are the plasmids pTS20, pTS21 and pTS22.

The advantages and the field of application will be readily appreciated from the following detailed description of the invention.

DETAILED DESCRIPTION OF THE INVENTION

It was surprisingly found that expression of a bacterial $\beta$-glucuronidase (GUS) reporter gene in transgenic *Petunia hybrida* plants, under the control of a hybrid promoter, comprising an anther box derived from the CHS-A promoter from *Petunia hybrida* fused to the CaMV 35S promoter (herein after referred to as the AB/CaMV 35S promoter) resulted in significantly higher expression in anthers versus corolla tissue, when compared to GUS expression driven by the CaMV promoter. Also the cell-type specificity was changed, since expression was observed in the tapetum cell-layer as well. This was not obtained with the 35S promoter without the anther box.

Apparently, the anther box is capable of driving anther-specific expression without the presence of additional cis-acting elements which are present in the CHS-A gene, as was formerly believed. The hybrid promoter is not anther-specific, since expression is detected in other tissues as well. The anther box is capable of driving expression in the tapetum cell-layer as well.

In a similar experiment as described for the GUS-reporter gene, an antisense-CHS gene (cDNA) from Petunia was placed under the control of an AB/CaMV 35S promoter, and this construct was used for the transformation of the purple flowering Petunia VR hybrid. After selection of transformed plants which expressed the construct, and after the plants were allowed to flower, it was found that the anthers of some of these plants were white instead of purple. White anthers had never been obtained in earlier experiments, in which the antisense CHS-A gene was fused to the normal 35S promoter controlling antisense-CHS expression, although the antisense gene was indeed expressed in the anthers.

Thus it is concluded that an anther box as defined herein can function to drive expression in the tapetum cell-layer of any gene (or antisense gene) in anther tissue, if this anther box is inserted into a high-level promoter, the origin of which is not critical. Moreover, it is even shown that the level of expression of an inhibitory gene in anther tissue is sufficiently high to inhibit expression in the anther tissue of a target gene.

Surprisingly, upon an attempt to self-fertilize transgenic *Petunia hybrida* plants having white anthers, it appeared that they were entirely male-sterile. Natural mutants lines of Petunia exist in which no functional chalcone isomerase enzyme is present. Chalcone isomerase is involved in the conversion of chalcones into flavanones, i.e. one step further in the flavonoid biosynthetic route. It is known that these plants are male-fertile. Thus, it can be concluded that, in order for obtaining male-sterile plants according to the proposed method, the target gene must be chosen from the group of genes encoding enzymes involved in the biosynthesis pathway leading to chalcone, as long as inhibition of these genes is not lethal to the plant as a whole.

In other experiments in which the Petunia antisense-CHS-A gene was placed under the control of the normal CaMV 35S promoter, it was established that the antisense-CHS construct can be used as inhibitory gene to inhibit expression of the corresponding target genes in corollas of tobacco and potato as well. This proves that the antisense approach also works in heterologous systems, and strongly suggests that male-sterile plants of different species can be obtained if transformed with the antisense-CHS gene from Petunia under the control of a AB/35S promoter.

Hence, new methods are provided for obtaining nuclear encoded male-sterile plants, which can be suitably used for the production of hybrid seeds. Thereto, plants of a selected variety are genetically transformed by introducing into cells of the said plants one or more recombinant polynucleotides, essentially comprising one or more inhibitory genes, which upon proper expression in the anthers of the plant, are capable of inhibiting expression of one or more genes encoding one or more enzymes involved in chalcone biosynthesis.

Generally, male-sterile plants are obtained by inhibiting the expression of a suitable target-gene encoding a chalcone biosynthetic enzyme, by proper expression of an inhibitory gene directed against that target-gene. Suitable target-genes can be selected from any of the genes that encode enzymes involved in the biosynthesis of chalcones, or its immediate precursors, as long as inhibition of a gene of this group does not negatively affect other desired characteristics of the variety. Generally, target-genes may be selected from the genes encoding enzymes that convert precursors of a chalcone, such as cinnamate 4-hydroxylase (C4H; E.C. 1.14.13.11), preferably 4-coumaroyl-CoA ligase (4CL; E.C. 6.2.1.12), most preferably the enzyme chalcone synthase (E.C. 2.3.1.74.), which directly converts its substrate into chalcone.

Inhibitory genes can be suitably selected from a range of alternatives, including sense and antisense genes, as illustrated in more detail below. Suitable sense inhibitory genes may for instance encode a ribozyme, directed against the RNA-product of the target-gene, or a (monoclonal) antibody directed against the gene product of the target-gene, or a selective protein inhibitor of the target-enzyme, if available. Alternatively the inhibitory gene may comprise a sense gene which is essentially identical to the target-gene, which upon proper expression inhibits the target-gene according to a yet unknown mechanism referred to as sense-sense inhibition or co-suppression (International Patent Application WO90/11682, DNA Plant Technology inc.).

Preferably the inhibitory gene is an antisense gene directed against the target-gene. The antisense gene does not necessarily need to be entirely complementary to the target gene, as long as its length and homology is enough to provide for a suitably high inhibition. Thus, the antisense gene may be (partially) complementary to the 5'-end of the of the corresponding target gene, the 3'-end, or the middle part, or (partially) complementary to the entire corresponding target gene. With partially complementary is meant the situation wherein the antisense gene is not fully homologous to the corresponding target gene, which may be due to the fact that e.g. the antisense gene is heterologous (i.e. obtained from a different source) to the target gene and the like. The antisense gene may be entirely synthetic as well. All these variations with respect to the choice of the antisense gene are not critical to the invention as long as the level of homology, and/or the total amount of complementarity is sufficient to inhibit expression of the target gene.

Proper expression of the inhibitory gene according to the invention can be obtained by placing the inhibitory gene under the control of a hybrid promoter which comprises at least a promoter which is functional in plants, preferably derived from a high-level promoter, e.g. the CaMV 35S RNA (or derivatives thereof), and an anther box derived from a gene that is expressed in immature anther tissue of plants. Suitable representatives of an anther box can be obtained, inter alia, from a CHS-A gene, a CHS-J gene, a CHI-B gene, or a DFR-A gene, and the like.

Preferably the said anther box is inserted into a promoter in the region between −2000 and +1, more preferably between −1000 and +1, most preferably between −150 and −50. In an especially preferred embodiment the anther box is inserted at position −90 in the CaMV 35S promoter.

The choice of the source plant from which the anther box is derived is not critical as long as the anther box functions properly in the ultimate transgenic host. Generally, it is preferred, that homology of the used anther box is as high as possible with boxes that are known to enhance expression in the anthers of the host plant. Such an anther box may be suitably synthesized from a known sequence of an anther box occurring in the ultimate host plant, or any other plant, derived from a different plant source, or otherwise.

Generally, but not necessarily, the genetic material on which the inhibitory gene fused to the hybrid promoter according to the invention is located, in the form of either recombinant DNA or RNA, is introduced into the plant on a recombinant polynucleotide, either DNA or RNA, closely linked to a selectable or screenable trait, such as a herbicide or antibiotic resistance, in order to allow for early selection or recognition of transformed cells. Optionally, the use of such marker may be omitted, because the presence and expression of an inhibitory gene according to the invention can be screened for directly when the transgenic plants are flowering. Recombinant polynucleotides are usually maintained or multiplicated in bacteria in the form of plasmids or other replicons (e.g. inserted in viral DNA or RNA). Alternatively, recombinant polynucleotides can be multiplied in vitro, e.g. using the polymerase chain (PCR) reaction, well known to researchers in this area. The actual method is not crucial to the invention.

Introduction of recombinant polynucleotides into plant material can be done using several techniques which are all well within reach of the average skilled person in the field of plant biotechnology. The way of introduction of genetic material into cells of the host plant is not particularly relevant, as long as the method provides a reasonable chance of success, and likewise a reasonably predictable result. Such method does not necessary preclude the need for some degree of selection of the ultimately desired result. This is however common practice in the area of plant genetic engineering, and does not comprise undue experimentation. Some examples just listed for purposes of illustration are transformation of protoplasts using the calcium/polyethylene glycol method (Krens et al., 1982; Negrutiu et al, 1987), electroporation (Shillito et al., 1985), microinjection (Crossway et al., 1986), (DNA or RNA-coated) particle bombardment (Klein et al, 1987), infection with viruses and the like. Preferably, use is made of the natural DNA transfer system of Agrobacterium species. Within the Agrobacterium technology the use of the so-called binary vector (Bevan et al., 1984) system is preferred.

The use of suitable bacterial backgrounds for DNA transfer to plant cells, the choice of vectors, suitable selection markers, incubation conditions, culture media and necessary DNA cloning techniques, is all very well within reach of the average skilled worker. After selection and/or screening for the transformed plant material, the transformed material is regenerated into whole plants, using methods extensively described in the literature (vide e.g. Horsch et al., 1985). Any plant part which is amenable to transformation and regeneration may be used.

The transformation and/or regeneration method is itself not critical for the invention as long as introduction of the genetic material into the plant cell and stable integration of (a copy) of the genetic material into the genome of a plant cell can be obtained, and the said plant material is amenable to regeneration into a shoot that can be subsequently subjected to rooting (or grafting), resulting in the generation of a whole new plant. The choice of the technique will depend on the particular type of plant material used, and/or the preference of the skilled worker.

After transformed plants have been obtained, they can be evaluated for the presence of the desired properties and/or the extent to which the desired properties are expressed. A first evaluation may include the level of expression of the inhibitory gene and the extent to which the transgenic plants are male-sterile. Subsequently transgenic plants can be selected that show stable and/or predictable inheritance of the male-sterile trait, and the like. Subsequently the (heterozygous) male sterile plants can be used directly for the production of hybrid seed, or alternatively be selfed with rescued pollen in order for obtaining homozygous male-sterile plants. Alternatively, homozygous male-sterile plants can be obtained by selfing male-sterile plants with viable but sterile pollen by (a) contacting the pistil of a male-sterile plant with pollen of the same male-sterile plant in the presence of a suitable flavonoid compound, and (b) allowing the pollen to germinate on the pistil and fertilize the male-sterile plant, and (c) allow the plant to set seed.

It may be possible to allow the immature pollen to further mature in the presence of chalcones prior to use in self-pollination of the male-sterile mother plant.

Especially preferred flavonoid compounds in the method are quercetin, kaempferol, and myricetin. The flavonoid compound can be suitably added to a conventional pollen medium, such as 'BK-medium', to an end concentration of about 10 nm to 10 $\mu$M, preferably of about 100 nM to 3 $\mu$M. The optimal concentration may vary from compound to compound and from species to species; putatively even from the extent to which the production of endogenous flavonoid compounds is inhibited in the male-sterile plant. However, in view of the general teaching given herein, suitable flavonoid concentrations can be determined for different situations without undue experimentation. Obviously, the advantage of having a few homozygous male-sterile plants enables one to rapidly obtain large amounts of heterozygous male-sterile seed which can be directly used for large scale production of hybrid seed.

The invention can be practised in any plant capable of self-pollination, for which there is an interest in the production of hybrid seeds.

In a second aspect of the invention a method is provided for obtaining homozygous male-sterile plants, by selfing the heterozygous male-sterile plants according to the invention, with pollen, the development of which is rescued due to the temporary presence of chalcone in the immature anthers of the plant, thereby overcoming the inhibition of in vivo chalcone synthesis. One embodiment of this aspect of the invention comprises administration of chalcones to compensate for the effect of inhibition of gene expression. A slightly different embodiment comprises compensation of inhibition of gene expression by allowing (temporary) in vivo production of chalcones. This can be achieved by introducing in addition to the inhibitory gene, a restoration gene under the control of an inducible promoter, in order to be able to control the expression of the restoration gene externally by adding an appropriate inducer. Preferably such restoration gene comprises e.g. a fusion gene at least comprising a part of the target gene, that is capable upon expression of inhibiting the effect of expression of the antisense gene, by complementary association to the antisense transcript (vide e.g. Robert et al., 1990).

Inducible restoration of fertility, as indicated shortly above, is also necessary in hybrid crops in which the commercial value lies in the seed or fruit. Obviously, male-sterility must then be lifted to allow pollination in the field, in order for obtaining seed or fruit. Such restoration may be for instance be invoked by administration of the inducer to the crop in the field, resulting in a sufficiently high expression of the restoration gene, in order to achieve neutralization of the antisense transcript.

ADVANTAGES

In contrast to many of the former methods to provide nuclear encoded male-sterile plants, the present method does not necessarily involve expression of genes which encode products that are toxic to somatic cells, such as DNAses, RNAses, or proteases. As a consequence, there is no need for a strict developmental or tissue-specific expression, as long as expression is obtained in anthers.

Male-sterile plants according to the invention are highly sterile and appear entirely female-fertile.

Furthermore, during the large scale production of hybrid seeds in the field or green house, male fertile plants, i.e. putative self-pollinators, can be discerned from male-sterile plants, which produce the hybrid seeds, on the basis of altered anther pigmentation. Subsequently, the self-pollinators can be separated, or destroyed, or if desired, their non-hybrid seed can be harvested separately.

Another advantage of methods according to the present invention is the ability for obtaining homozygous male-sterile plants, which offer great advantages in the maintenance and propagation of a heterozygous male-sterile parental line. Only a few homozygous plants are needed, which because of their limited number can be propagated in vitro by techniques well known in the art. The homozygous male-sterile line is cross-fertilized with a male-fertile parental line, and subsequently the heterozygous male-sterile seed is used for the large scale-production of hybrid crops in the field. Of the corresponding hybrid seed, 50% will be male-sterile and 50% male-fertile. In case this ratio is not sufficient for obtaining a high yield of commercial product (i.e. seed or fruit) by self-fertilization, this ratio can be ameliorated by partial restoration of male-sterility by administration of an inducer to activate expression of the restoration gene.

EXPERIMENTAL

DNA-methodology

DNA isolation, subcloning, restriction analyses and sequencing were performed using standard procedures well known to persons skilled in the art, vide e.g. Maniatis et al., 1982. Isolation of DNA from individual petunia transformants and DNA gel blot analysis were performed as described by Koes et al., 1987.

GUS extractions and fluorometric and histochemical GUS assays

Fresh material was collected from the transgenic plants and used for the GUS assays. GUS extractions were performed as described by Jefferson et al., (1987), by grinding the tissue with liquid $N_2$ and Dowex-1 (Sigma). Fluorometric GUS activity measurements were performed according to Jefferson et al., (1987). Fluorescence values were corrected for quenching of the extract by measuring the increase in fluorescence after addition of a known amount of 4-methylumbelliferyl. Protein concentrations were determined using the Bio-Rad protein assay with bovine serum albumin as a standard.

Histochemical localization of GUS activity was performed as described by Koes et al. (1990). Before staining, anthers were cut, in two with a razor blade. To eliminate background GUS activity in anthers X-gluc staining solution was used of pH 8.0.

To exclude artifacts, which can result from differences in cell size, penetration of substrate into the tissue, and background enzyme activity, we repeatedly performed the histochemical assays on anthers of transgenic and untransformed plants. For analysis at the single cell level, X-gluc-stained tissues were fixated and imbedded in paraffin according to Koes et al., (1990). Using a microtome, 7 μm thick sections were cut of which photographs were taken by light-field microscopy.

Detection of flavonoids

Anthers of ten buds were incubated in 1 ml 2M HCl for 16 hr after hydrolysis (20 min at 100° C.) flavonoids were extracted in a small volume of isoamylalcohol and separated on cellulose TCL plates using acetic acid: hydrochloric acid: water (30:3:10) as eluent.

Isolation of RNA and RNAase protection

Anthers of 5–7 buds (size 40–50 mm) were used for isolation of RNA as described by Koes et al., (1989). Endogenous CHS mRNA was detected by RNAse protection assays, performed according to van Tunen et al., (1988), using a full size CHS(A) cDNA cloned in pTZ18U as a probe (Koes et al., 1989).

In vitro pollen germination

Plants were grown at 18–22° C. under standard greenhouse conditions. Pollen was collected from flowers at anthesis and germinated on solidified medium containing 3 mM $H_3BO_3$, 1.7 mM $Ca(NO_3)_2$, 10% sucrose, 0.7% agar, pH 5.8. Pollen was incubated for 2 hr at 24° C. in the dark and stained with 1% acetocarmine as described by Bino et al., (1987).

EXAMPLES

I Construction of chimeric GUS-genes

Figure 2:
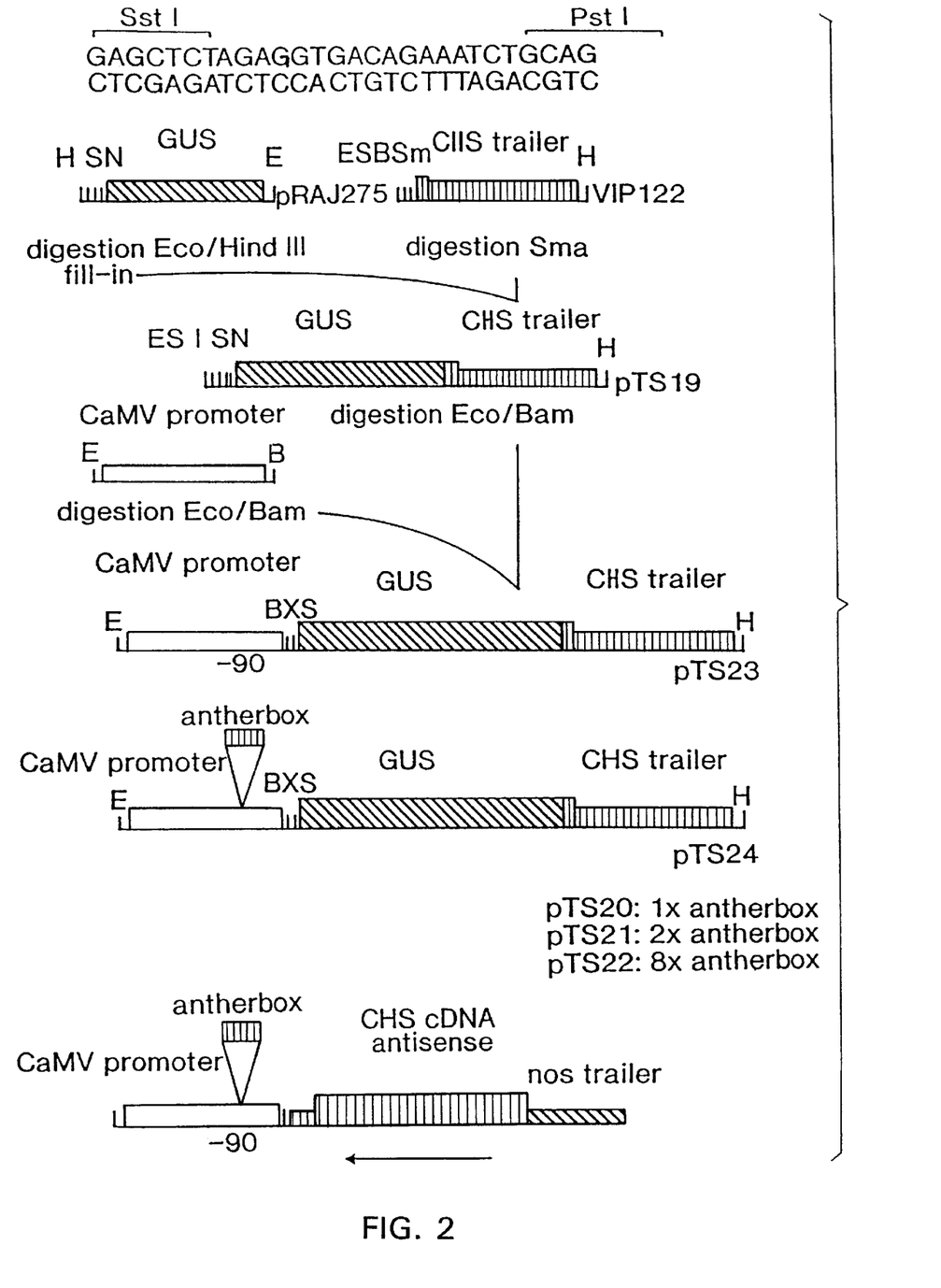
FIG. 2 is a diagrammatic representation of the different cloning steps for obtaining the chimeric GUS-constructs or the chimeric antisense-CHS constructs.
Figure 3:
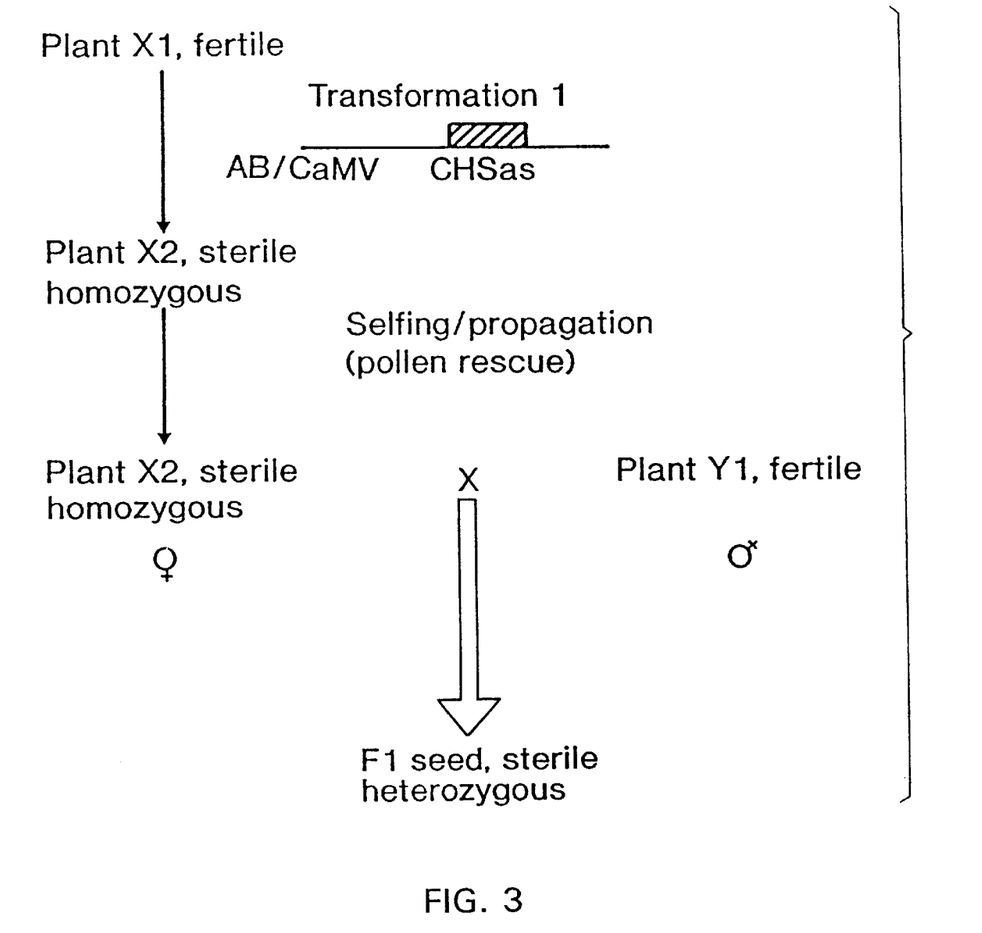
FIG. 3 is a diagrammatic presentation of a method for obtaining hybrid seed which is male-sterile; this hybrid seed can be used for crops of which no setting of seed or fruit is required; X female parental variety; Y=male parental line; CaMV=cauliflower mosaic virus 35S promoter; AB=anther box, inserted into the 35S promoter; CHSas=antisense chalcone synthase gene.
Figure 4:
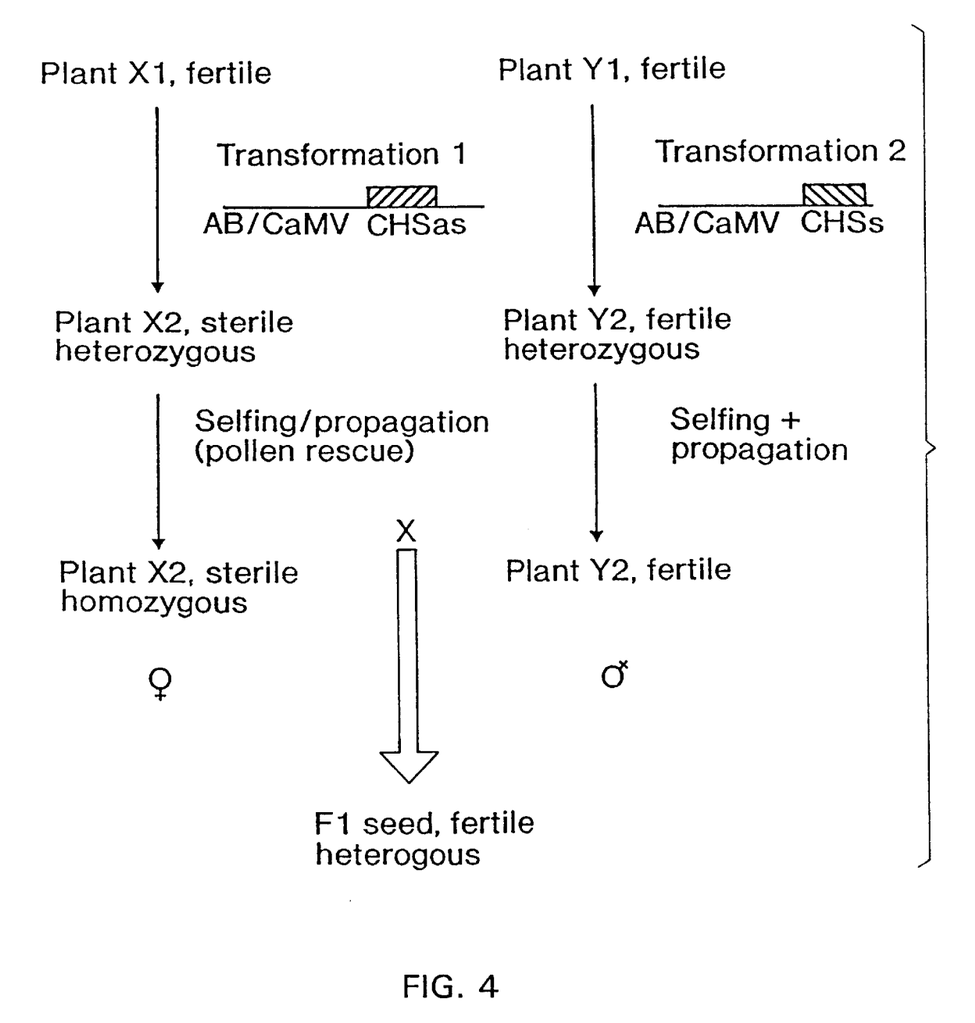
FIG. 4 is a diagrammatic presentation of a method for obtaining hybrid seed which is male-fertile; this hybrid seed can be used for crops of which setting of seed or fruit is essential; CHSs sense (normal) chalcone synthase gene; all other indications as in FIG. 3.
Figure 5:
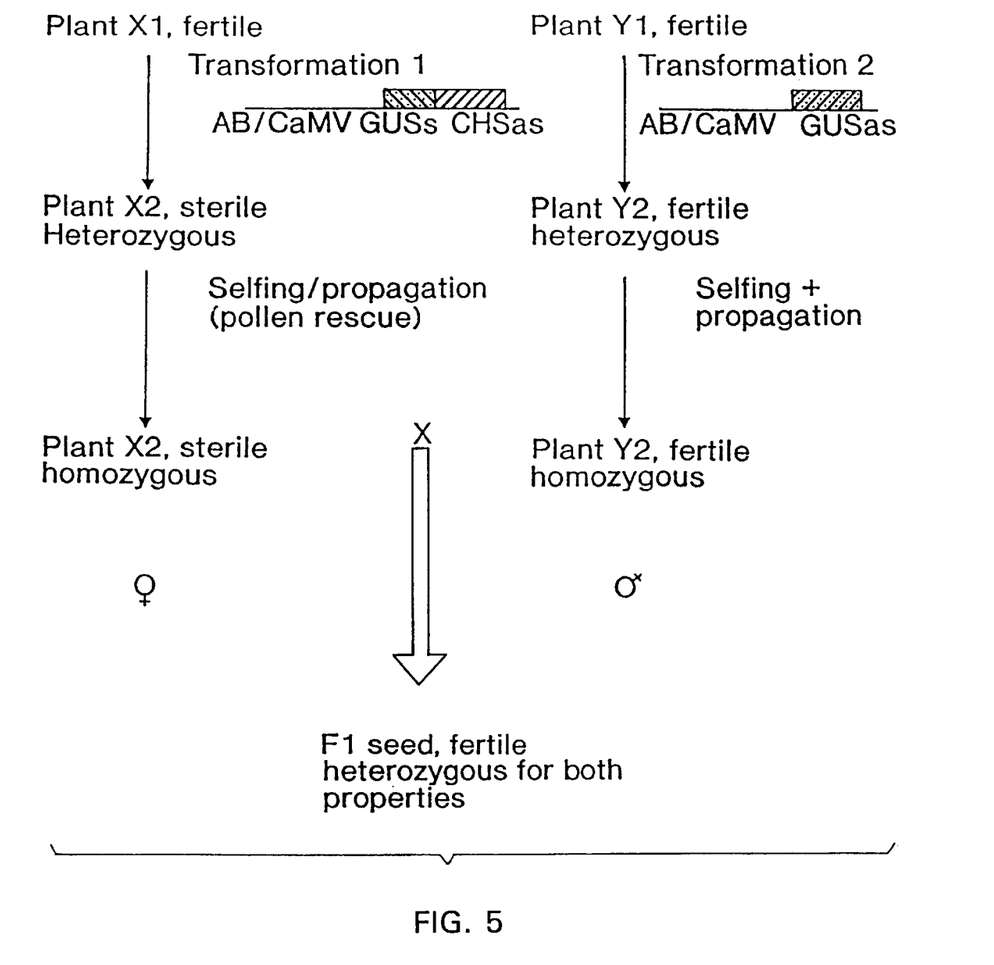
FIG. 5 is a diagrammatic presentation of a method for obtaining hybrid seed which is male-fertile; this hybrid seed can be used for crops of which setting of seed or fruit is essential; GUSs=$\beta$-glucuronidase gene of *E. coli*; the GUSs and the CHSas gene are physically coupled as to form a fusion gene; all other indications as in FIG. 3.
Figure 6:
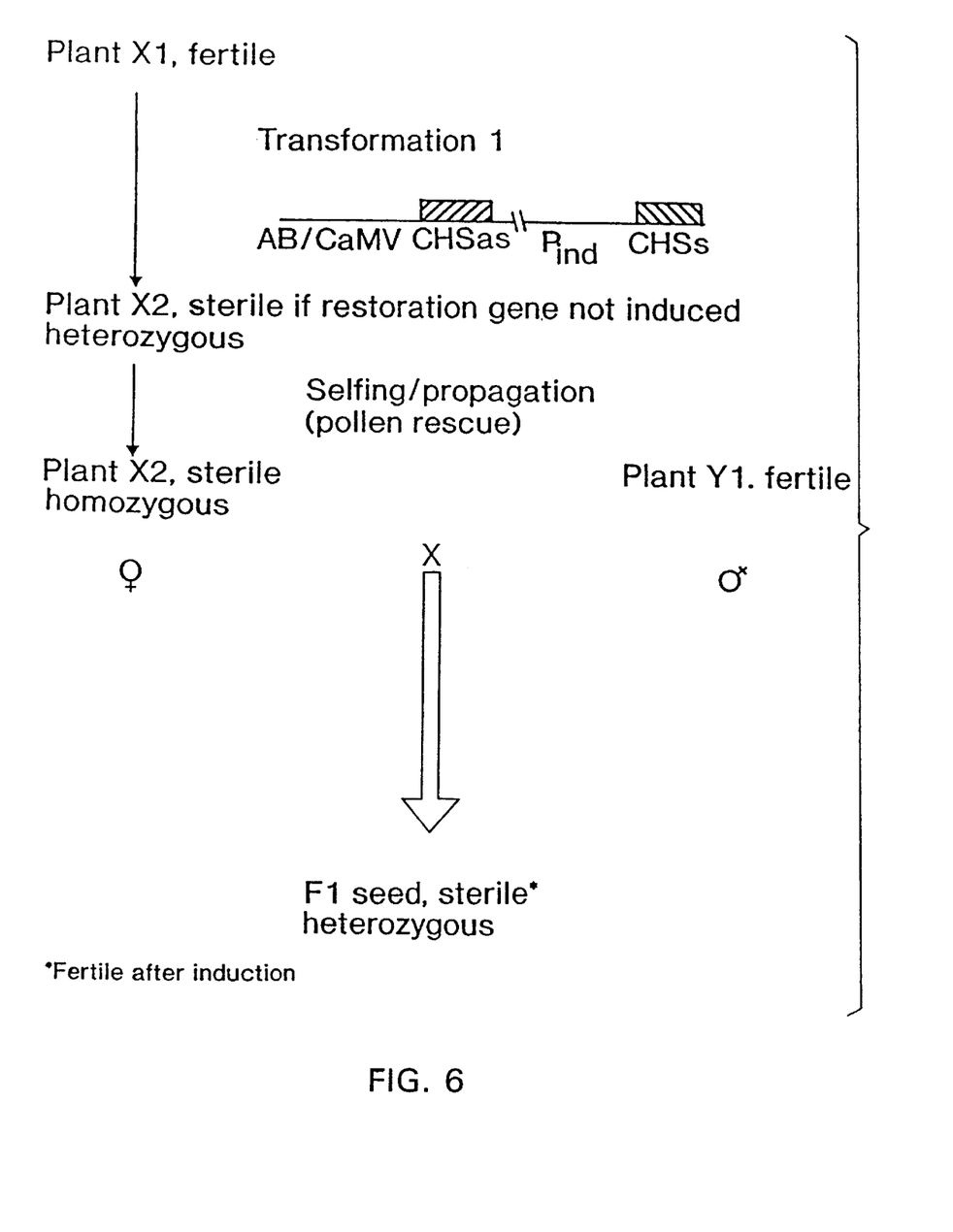
FIG. 6 is a diagrammatic presentation of a method for obtaining hybrid seed which is inducible male-fertile; this hybrid seed can be used for crops of which setting of seed or fruit is essential; all indications are as in the above Figures.
Figure 7:
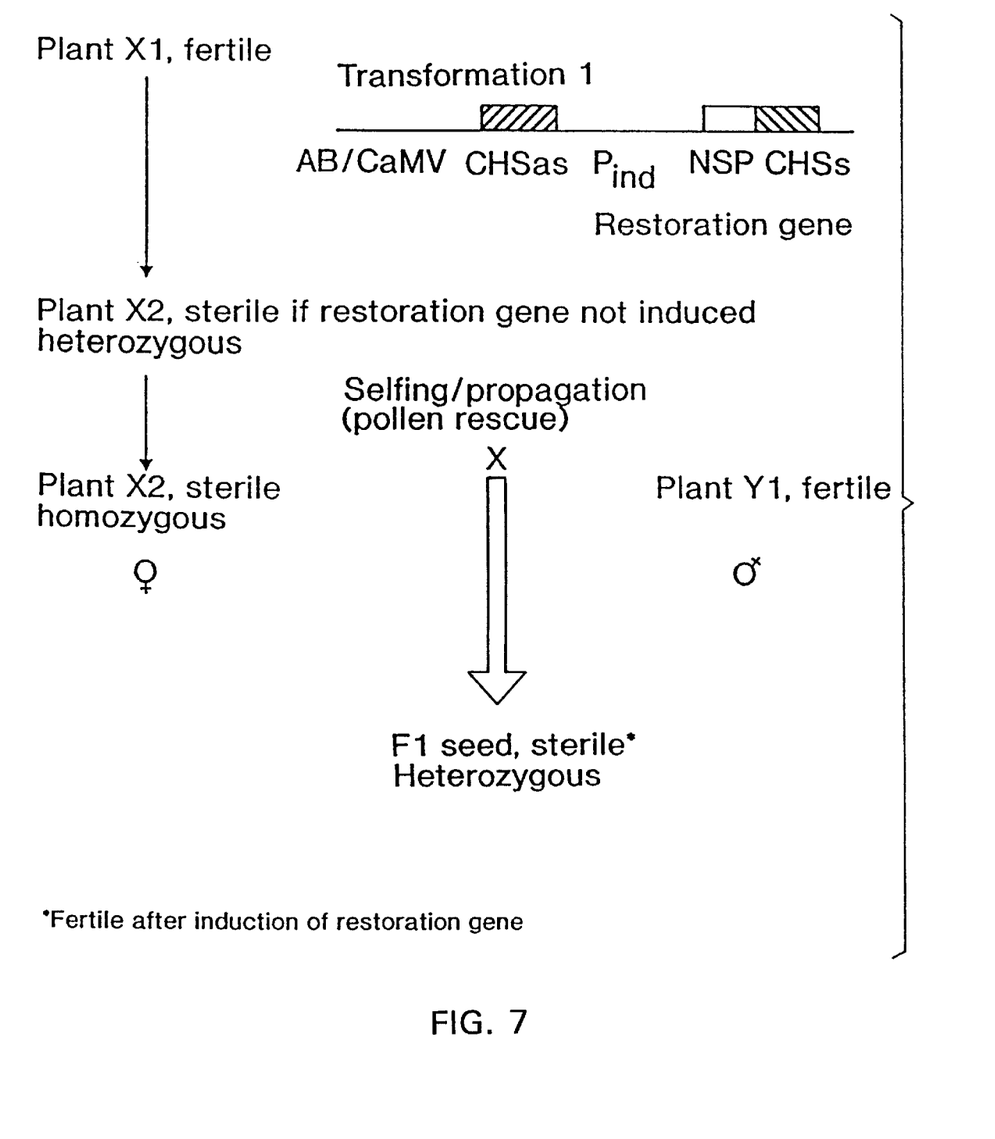
FIG. 7 is a diagrammatic presentation of a method for obtaining hybrid seed which is inducible male-fertile; this hybrid seed can be used for crops of which setting of seed or fruit is essential; NSP=nonspecific part of the restoration gene to avoid a putative co-suppressive effect of the CHSs part of the restoration gene; all other indications are as in the above Figures.

The chimeric GUS constructs were generated by cloning the GUS coding region of pRAJ 275 (Jefferson et al., 1987) as an EcoR/HindIII fragment, filled in with klenow polymerase, in the SmaI site of VIP122 that contains the CHS(A) tail (van der Meer et al., 1990), resulting in pTS18. The clone pTS18 was ligated in the plasmid pTZ18R (Promega) as a SalI/HindIII fragment, yielding pTS19. The CaMV 35S promoter of VIP102 (van der Krol et al., 1988), digested with EcoRI and BamHI was inserted in pTS19 cut with EcoRI and BamHI resulting in pTS23 (see also FIG. 2). The oligonucleotides 5'-GAGCTCTAGAGGTGACAGAAATCTGCAG-3' (SEQIDNO: 6) and 5'-CTGCAGATTTCTGTCACCTCTAGAGCTC-3' (SEQIDNO: 7) were allowed to anneal to each other, 5' phosphorylated using T4 kinase and cloned in pTS23 digested with EcoRV yielding pTS24. The orientation of the inserted antherbox was determined by partial digestion of one of both restriction sites flanking the anther box and running the end-labelled fragments on a sequence gel. All chimeric GUS-constructs were inserted as EcoRI/HindIII fragments into the binary vector Bin 19 (Bevan, 1984).

II Construction of chimeric antisense-CHS genes

The same synthetic anther box was also cloned at the EcoRV site in the CaMV promoter of VIP102, containing the CaMV-antisense-CHS(A)-nos construct; van der Krol et al., 1988). The orientation and the number of cloned anther boxes were determined as described in Example I. The following antisense-CHS(A) constructs were introduced in petunia plants: pTS20 (with a single anther box in the normal orientation), pTS21 (with two copies of the anther box in the reverse orientation) and pTS22 (with eight copies of the anther box in the normal orientation). All chimeric antisense-CHS(A) constructs were inserted as EcoRI/HindIII fragments into the binary vector Bin 19 (Bevan, 1984).

III Transformation of Petunia plants

The binary vectors containing the GUS-constructs (pTS23, containing the normal CaMV 35S promoter; pTS24, containing the hybrid AB-CaMV 35S promoter) or the antisense-CHS(A) constructs (pTS20; pTS21; pTS22) were transferred from E. coli JM83 (Messing, 1978) to Agrobacterium tumefaciens strain LBA 4404 (Hoekema, et al., 1983) by triparental mating (Rogers et al., 1986), using a strain containing plasmid pRK2013 (Ditta et al., (1980). Exconjugants were used to transform Petunia hybrida leaf discs, as described by Horsch et al., (1985). Leaf discs were prepared from top leaves of young, non-flowering plants. Petunia hybrida variety W115 was used in transformation experiments with the GUS-constructs and the petunia VR hybrid was used for the antisense-CHS(A) constructs. After shoot and root induction on kanamycin-containing media, plants were put on soil and transferred to the greenhouse. Plants regenerated (on kanamycin-free media) from leaf discs treated with the LBA4404 strain lacking a binary vector served as a control.

IV Analysis of transgenic plants expressing the GUS constructs

To study the influence of the anther box on regulation of gene expression, transgenic plants carrying the GUS-constructs were analyzed for expression patterns using the methods described in the Experimental part.

About 25 independent transgenic petunia plants containing the AB/CaMV 35S-GUS construct and 25 petunia plants containing the control CaMV-GUS construct were analyzed. Because the expression level of an introduced gene can differ between independent transformants due to the so-called position effect (Weising et al., 1988), the GUS activity of the exogenous gene in corolla was used as an internal standard in the measurement of the activity found in anthers for each individual transformant. The average ratio (i.e. from all the plants taken together) for the plants containing the hybrid promoter construct were higher than the average ratio of the control promoter construct. To check whether this was significant, all separate measurements were analyzed with the Wilcoxon rank test. With an $\alpha<0.05$, the GUS activity in anthers versus corolla was significantly higher in transformants containing the AB/CaMV 35S-promoter GUS construct compared to transformants containing the control CaMV construct. The presence of the anther box enhances CaMV driven GUS activity in anthers compared to the activity in corolla with factor 3.

In order to determine whether the insertion of the anther box sequence within the CaMV promoter alters its expression in anthers in a qualitative way, the cell type specific GUS expression was monitored histochemically (vide: Experimental part). In cross-sections, a petunia anther comprises (from inside to outside) a vascular cylinder surrounded by parenchymatic cells of the connectivum, four loculi containing the sporogenic tissue (pollen), and the endothecium. Each of the loculi is surrounded by a layer of specific cells (tapetum) that functions in the nourishment of sporogenic cells. In late stages of anther development, the loculi are disrupted at the stomium and the pollen grains are released.

Cross-sectioned anthers of multiple independent CaMV-GUS transformants were incubated with the GUS substrate X-gluc, and showed a strong blue colour, representing GUS activity, in almost all different cell types of the anther. The CaMV promoter drives GUS activity in the vascular cylinder, connectivum and the endothecium, but no GUS activity was observed in tapetum cells. Staining was not observed in anthers of untransformed control plants at pH 8.0. If the pH of the staining buffer was reduced to 7, background staining could be observed in untransformed anther tissue, therefore, all staining experiments were performed at pH 8.0. Examination of the CaMV-GUS transformed anthers at single cell level showed that the CaMV-GUS transformed anthers exhibit blue precipitation in all cell types except for the tapetum cells. Histochemical analysis of multiple independent transformants expressing GUS genes driven by the AB/CaMV 35S promoter showed a slightly different GUS staining pattern compared to the normal CaMV-GUS expressers. In addition to the normal CaMV-GUS staining pattern there is a clear blue staining of the tapetum cells. The blue precipitation in the tapetal cells is even more distinct at single cell level. Both the fluorometric and histochemical GUS assay show a clear effect of insertion of the anther box in the CaMV promoter not only at the level of GUS expression but also at the cell type specificity of GUS expression driven by this hybrid promoter.

V Analysis of transgenic plants expressing the antisense-CHS(A) constructs

Thirty five independent petunia (VR hybrid) transformants were obtained in total, of which 5 plants yielded flowers with a reduced anther pigmentation. There was no correlation between inhibition of corolla pigmentation and inhibition of anther pigmentation. Every combination of pigmented or non-pigmented anthers with normally pigmented corollas, or corollas with a reduction of pigmentation was found. With all three constructs used for transformation (i.e. pTS20; pTS21; pTS22) white anthers could be obtained. Inhibition of anthers therefore, seems to be independent of the number and orientation of the inserted anther box. Transformation of petunia VR hybrid with the pTS20 construct (one copy of the anther box in the normal orientation) resulted in 11 independent transgenic plants of which 5 plants showed a normal phenotype, 5 plants showed reduced pigmentation of the corolla and one plant yielded flowers with coloured corolla and white anthers. Transformation with pTS21 (two copies of the anther box in reverse orientation) resulted in 15 independent transformants of which 9 plants showed no effect; 5 plants gave rise to flowers with reduced corolla pigmentation of which 2 also had white anthers; one transformant showed wild type coloured flowers with white anthers. Of the nine independent transformants containing pTS22 (with 8 copies of the anther box in the normal orientation), 7 plants had a wild type phenotype; one plant showed flowers with reduced corolla pigmentation and one plant bore flowers with white anthers and normally coloured corollas.

In order to examine whether the reduction of anther pigmentation resulted from reduction of CHS mRNA level in anthers, total RNA was isolated of white anthers and purple coloured anthers and analyzed with a RNAase protection method. In this protection experiment, using $^{32}$P-labelled antisense V30-CHS RNA as probe, the endogenous VR CHS transcripts are digested in four subfragments. Inhibition of anther pigmentation showed to be accompanied by a specific reduction of CHS steady state mRNA level in anthers.

Surprisingly, in course of self-crossing the transgenic plants for linkage analysis it became clear that the white pollen are sterile. Transformants with nonpigmented anthers failed to produce mature, healthy looking seed pools after self-pollination. Only very occasionally some seeds were formed, but these did not germinate.

To determine at which stage of anther (and pollen) development white pollen grains start to degenerate, cross-sectioned white anthers and pollen of different developmental stages were analyzed under the microscope. The development of the white anthers did not deviate much from the normal petunia anther development. The pollen grains however, showed an arrest in development after the tetrad, i.e. the early microspore, stage. In vitro germination of pollen derived from white anthers, showed that no pollen tubes were formed.

This early stage in pollen development coincides with the onset of flavonoid gene expression. These data indicate to a putative function of flavonoids in pollen development at the early binucleate stage. Hence it can be concluded that rescue of pollen development, e.g. by inducing the synthesis of a restoration gene, should start at about this stage.

To ensure F1 material the male-sterile transformants with white anthers were pollinated with the petunia variety V30. The male-sterile plants were completely female-fertile.

Analysis of the progeny of the primary transformants established that the introduced traits were stable, and could be inherited by the progeny in a predictable fashion. A petunia sterile transformant with white pollen was crossed with *Petunia hybrida* (V30) and the F1 progeny was both analyzed on the 'white pollen' phenotype and on the presence on an insert on Southern blot. DNA was extracted from leaves of several progeny plants and Southern blot analysis showed a complete co-segregation of the antisense phenotype with one insert.

EXAMPLE VI

Self-Fertilisation of Male-Sterile Plants

Sterile petunia pollen was taken from moderate expressers of antisense-chs plants and used for self-pollination in combination with the flavonols quercetin, kaempferol or myricetin. These plants were selected on the basis of the presence of a small number (less than 1%) viable immature pollen; these pollen can be made to mature in vitro. The sterile pollen were put in normal pollen medium (BK-medium: 100 mg/l $H_3BO_3$ 300 mg/l $CaNO_3$, 200 mg/l $MgSO_4$, 100 mg/l $KNO_3$, 12.5% sucrose in sterile water)

supplemented with quercetin, myricetin or kaempferol to an end concentration ranging from about 100 nM to 3 μM then pipetted onto the pistils of male-sterile mother plants.

The flavonoid compounds are effective in the range indicated above; the optimal concentration cannot be given since this varied heavily with the individual male-sterile plant used; probably, this can be explained by the fact that some anti-chs plants still produce a small amount of chalcone synthase, which obviously effects the concentrations of flavonoid compounds present in the reproductive organs. After pollination seedset was observed and the seeds were harvested. The seeds germinated normally and full grown plants were obtained from these seeds.

Upon attempt to self-pollinate these plants it was found that they were still male-sterile. These plants can be used as homozygous mother plants in a crossing with a male-fertile donor in order to rapidly obtain large amounts of heterozygous male-fertile plants for the production of hybrid seed.

It is expected that since the compounds used to overcome sterility of the pollen are flavonols, occurring in many plants, extracts of for instance pistils, corolla tissue and putatively mentor pollen (pollen made sterile through irradiation) from normal plants may also be used to supplement pollen derived from a male-sterile plant according to the invention.

REFERENCES

Beld, M. G. H. M., Martin, C., Huits, H., Stuitje, A. R., and Gerats, A. G. M. (1989). Flavonoid synthesis in petunia: Partial characterization of dihydroflavonol-4-reductase genes. Plant Mol. Biol. 13, 491–502.

Bevan M. (1984). Binary Agrobacterium vectors for plant transformation. Nucl. Acids Res. 12, 8711–8712.

Bino, R. J., Hille, J., and Franken, J. (1987) Kanamycin resistance during in vitro development of pollen from transgenic tomato plants. Plant Cell Rep. 6, 333–336.

Coe, E. H., Jr., McCormick, S. M., and Modena, S. A. (1981). White pollen in maize. J. Hered. 72, 318–320.

Ditta et al., (1980), Proceeding of the National Academy of Sciences USA, 12, 7347–7351.

Dixon, R. A. (1986). the phytoalexin respons: Eliciting, signalling and control of host gene expression. Biol. Rev. 61, 239–291.

Hedin, P. A., and Waage, S. K. (1986). Roles of flavonoids in plant resistance to insects. In Progress in Clinical and Biological Research. Vol. 213: Plant Flavonoids in Biology and Medicine. V. Cody, E. Middleton Jr., and J. B. Harborne, eds (New York: Alan R. Liss), pp. 87–100.

Hoekema, A. et al., (1983), Nature 303: 179–180.

Horsch, R. B., Fry, J. E., Hoffmann, N. L., Eichholtz, D., Rogers, S. G., and Fraley, R. T. (1985). A simple and general method for transferring genes into plants. Science 227, 1229–1231.

Jacobs, M., and Rubery, P. H. (1988). Natural occuring auxin transport regulators. Science 241, 246–349.

Jefferson, R. A., Burgess, S. M. and Hirsh, D. (1986). Proc. Natl. Acad. Sci. USA 83, 8447–8451.

Jefferson, R. A., Kavanagh, T. A., and Bevan, M. W. (1987). Gus fusions: β-Glucoronidase as a sensitive and versatile gene fusion marker in higher plants. EMBO J. 6, 3901–3907.

Koes, R. E., Spelt, C. E., Mol, J. N. M., and Gerats, A. G. M. (1987). The chalcone synthase multigene family of *Petunia hybrida* (V30): Sequence homology, chromosomal localization and evolutionary aspects. Plant Mol. Biol. 10, 375–385.

Koes, R. E., Spelt, C. E. and Mol, J. N. M., (1989). The chalcone synthase multigene family of *Petunia hybrida* (V30): Differential, light-regulated expression during flower development and UV light induction. Plant Mol. Biol. 12, 213–225.

Koes, R. E., van Blokland, R., Quattrocchio, F., van Tunen, A. J., and Mol, J. N. M. (1990). Chalcone synthase promoters in petunia are active in pigmented and unpigmented cell types. Plant Cell 2, 379–392.

Koltunow A. M., Truettner, J. Cox, K. H., Wallroth, M., and Goldberg, R. B. (1990). Different termporal and spatial gene expression patterns occur during anther development. Plant Cell 2, 1201–1224.

Lamb, C. J., Lawton, M. A., Dron, M., and Dixon, R. A. (1989). Signals and transduction mechanisms for activation of plant defenses against microbial attack. Cell 56, 215–224.

Long, S. (1989). Rhizobium-legume nodulation: Life together in the underground. Cell 56, 203–214.

Maniatis, T., Fritsch, E. F., and Sambrook, J. (1982). Molecular Cloning: A Laboratory Manual (Cold Spring Harbor, N.Y.: Cold Spring Harbor Laboratory).

Mariani, C., De Beuckeleer, M., Truettner, J., Leemans, J., and Goldberg, R. B. (1990). Induction of male sterility in plants by a ribonuclease gene. Nature 347, 737–741.

Messing, J., (1978) Recombinant DNA Technical Bulletin NIH Publication No. 79–99, 2, 43–48.

van der Krol, A. R., Lenting, P. J., Veenstra, J. G., van der Meer, I. M., Koes, R. E., Gerats, A. G. M., Mol, J. N. M., and Stuitje, A. R. (1989). An 'antisense chalcone synthase gene' in transgenic plants inhibits flower pigmentation. Nature 333, 866–869.

van der Meer, I. M., Spelt, C. E., Mol, J. N. M., and Stuitje, A. R. (1990). Promoter analysis of the chalcone synthase (chsA) gene of *Petunia hybrida*: A 67 bp promoter region directs flower-specific expression. Plant Mol. Biol. 15, 95–109.

van der Meer, I. M. Stuitje, A. R., and Mol., J. N. M. (1991). Regulation of general phenylpropanoid and flavonoid gene expression. In Control of Plant Gene Expression. D. P. S. Verma, ed. (The Telford Press, Caldwell, New Yersey), in press.

Plegt, L., and Bino, R. J. (1989). β-Glucoronidase activity during development of the male gametophyte from transgenic and non-transgenic plants. Mol. Gen. Genet. 216, 321–327.

Robert L. S. et al., (1990) Bio/Technology 8, p. 459.van

Rogers et al., (1986), Methods in Enzymology 118, 627–641).

Schmelzer, E., Jahnen, W., and Hahlbrock, K. (1988). In situ localization of light-induced chalcone synthase mRNA, chalcone synthase, and flavonoid endproducts in epidermal cells of parsley leaves. Proc. Natl. Acad. Sci. USA 85, 2989–2993.

Shillito, R. D. et al., (1985), Bio/Technology 3, 1099–1102.

Tunen, A. J. van, Koes, R. E., Spelt, C. E., van der Krol, A. R. Stuitje, A. R., and Mol, J. N. M. (1988). Cloning of the two chalcone flavanone isomerase genes from *Petunia hybrida*: Coordinate, light-regulated and differential expression of flavonoid genes. EMBO J. 7, 1257–1263.

van Tunen, A. J., Hartman, S. A., Mur, L. A. and Mol, J. N. M. (1989). Regulation of chalcone isomerase (CHI) gene expression in *Petunia hybrida*: The use of alternative promoters in corolla, anthers and pollen. Plant Mol. Biol. 12, 539–551.

Weising et al, (1988), Annu. Rev. Genet. 22, 241–277.

We claim:

1. A polynucleotide which can be directed against a target gene of a plant having reproductive organs which render the plant both male-fertile and female-fertile, said plant having a biosynthesis pathway wherein there is produced a plurality of enzymes which catalyze a stepwise synthesis of chalcone, said target gene encoding one enzyme of the chalcone biosynthesis pathway, said polynucleotide comprising:
   a) an inhibitory gene encoding an RNA molecule or polypeptide which, when produced in said plant at a sufficient level, inhibits expression of said one enzyme sufficiently to render the plant male-sterile without impairing the female-fertility of the plant; and
   b) a promotor operably linked to said inhibitory gene, said promotor being sufficiently active in anthers of the plant to promote expression of said RNA molecule or polypeptide in the anthers of the plant at said sufficient level.

2. A polynucleotide as claimed in claim 1 wherein the polynucleotide is a hybrid molecule that is formed by an in vitro combination of DNA from a plurality of different molecules.

3. A polynucleotide as claimed in claim 2 wherein the inhibitory gene encodes an RNA molecule that is sufficiently complementary to and capable of hybridizing with an RNA molecule produced by said target gene so as to inhibit expression of said one enzyme.

4. A polynucleotide as claimed in claim 2 wherein the inhibitory gene encodes an RNA molecule which is substantially identical to an RNA molecule produced by said target gene whereby it inhibits expression of said one enzyme by co-suppression.

5. A plant genome, comprising incorporated therein a polynucleotide according to claim 1.

6. A method for rendering a plant incapable of producing functional pollen, said method comprising inhibiting the synthesis of chalcone in cells of an anther of the plant, including cells of a tapetum layer of the anther, by a) transforming the plant with an inhibitory gene that encodes a nucleotide transcript that inhibits expression of a target gene, said target gene encoding a nucleotide transcript for an enzyme of the chalcone biosynthesis pathway, the transcript encoded by the inhibitory gene being sufficiently similar or sufficiently complementary to the transcript encoded by the target gene to inhibit the expression of the target gene by antisense inhibition or cosuppression, said inhibitory gene being under the control of a promoter that causes selective expression of the gene in the anther of the plant including the cells of the tapetum layer, such that expression of the gene renders the plant incapable of producing functional pollen but is not lethal to the plant; and b) regenerating the plant.

7. A method as claimed in claim 6 wherein said enzyme is chalcone synthase (CHS; E.C. 2.3.1.74).

8. A polynucleotide according to claim 3, wherein the target gene encodes chalcone synthase.

9. A polynucleotide according to claim 1 wherein said one enzyme is selected from the group consisting of cinnamate 4-hydroxylase (C4H; E.C. 1.14.13.11), 4-coumaroyl-CoA ligase (4CL; E.C. 6.2.1.12), and chalcone synthase (CHS; E.C.2.3.1.74).

10. A method for obtaining a male-sterile plant, comprising the steps of
   (a) transferring a polynucleotide according to claim 1 to cells of a male-fertile plant,
   (b) generating whole new plants from cells having incorporated said polynucleotide, and
   (c) selecting a plant that is male-sterile.

11. A plant cell comprising the plant genome of claim 5.

12. A male-sterile plant comprising the plant genome of claim 5.

13. A method for obtaining seed of the male-sterile plant according to claim 12, comprising the steps of:
   (a) contacting the pistil of a male-sterile plant with pollen of the same male-sterile plant in the presence of a suitable flavonoid compound, and
   (b) allowing the pollen to germinate on the pistil and fertilize the male-sterile plant, and
   (c) allowing the plant to set seed.

14. A method according to claim 13, wherein the pollen are suspended in a suitable pollen medium comprising a flavonoid compound selected from the group consisting of myricetin, quercetin and kaempferol, within a concentration range of 100 nm to 3 $\mu$M prior to contacting the pistil of a male sterile plant with the pollen.

15. A method according to claim 14, wherein the pollen medium has the following composition: 100 mg/l $H_3BO_3$ 300 mg/l $CaNO_3$, 200 mg/l $MgSO_4$, 100 mg/l $KNO_3$, 12.5% sucrose in sterile water.

16. Seed obtained by using a method according to claim 13, said seed containing said plant genome.

17. A homozygous male-sterile plant obtainable from a seed according to claim 16.

18. A method for the production of heterozygous male-sterile plants by fertilising a homozygous male-sterile plant according to claim 17 with a male-fertile plant, harvesting the seed and growing heterozygous male-sterile plants from said seed.

19. A method for obtaining hybrid seed comprising the steps of crossing a male-sterile plant from claim 12 with a male-fertile plant and collecting the hybrid seed.

20. The hybrid seed obtained by the method according to claim 19.

21. A male-sterile plant produced by the method of claim 6.

22. A method as claimed in claim 6, wherein the inhibitory gene is an antisense gene directed against the target gene.

23. A method for obtaining seed of a male-sterile plant comprising the steps of:
   a) obtaining a male-sterile plant by transforming a male-fertile plant with a DNA construct comprising a promoter that will promote expression in the anthers of the plant that is operably linked to a chalcone synthase gene, or a portion of said gene that is sufficient to inhibit the expression of chalcone synthase in the plant, and
   b) contacting the pistil of said male-sterile plant with pollen of the same male-sterile plant in the presence of a flavonoid compound selected from the group consisting of myricetin, quercetin and kaempferol, and
   c) allowing the pollen to germinate on the pistil and fertilize the male-sterile plant, and
   d) allowing the plant to set seed.

24. A DNA construct for use in transforming a male-fertile plant, said construct comprising a promoter that will promote expression in the anthers of the male-fertile plant, said promoter being operably linked to an inhibitory gene that is a) a chalcone synthase gene, or a portion of the chalcone synthase gene that is sufficient to inhibit the expression of chalcone synthase in the plant, or b) an antisense gene that is sufficiently complementary to a native gene in the male-fertile plant that encodes chalcone synthase to inhibit the expression of chalcone synthase in the male-fertile plant, said construct being a hybrid molecule that is not naturally present in said male-fertile plant.

25. A DNA construct as claimed in claim 24 wherein the inhibitory gene is the chalcone synthase gene or the portion of the chalcone synthase gene.

26. A method for obtaining a male-sterile plant, comprising the steps of:
   a) transferring the construct of claim 25 to a cell of a male-fertile plant so that the construct is incorporated into the genome of the cell, and
   b) generating a new plant from the cell having said construct incorporated into its genome.

27. A method for obtaining seed from the male-sterile plant of claim 26 comprising the steps of:
   i) contacting the pistil of the male-sterile plant with pollen of the same male-sterile plant in the presence of a flavonoid compound selected from the group consisting of myricetin, quercetin, and kaempferol,
   ii) allowing the pollen to germinate on the pistil,
   iii) allowing the plant to set seed, and
   iv) collecting the seed.

28. A DNA construct as claimed in claim 24 wherein the inhibitory gene is the antisense gene.

29. A method for obtaining a male-sterile plant, comprising the steps of:
   a) transferring the construct of claim 28 to a cell of a male-fertile plant so that the construct is incorporated into the genome of the cell, and
   b) generating a new plant from the cell having said construct incorporated into its genome.

30. A method for obtaining seed from the male-sterile plant of claim 29 comprising the steps of:
   i) contacting the pistil of the male-sterile plant with pollen of the same male-sterile plant in the presence of a flavonoid compound selected from the group consisting of myricetin, quercetin, and kaempferol,
   ii) allowing the pollen to germinate on the pistil,
   iii) allowing the plant to set seed, and
   iv) collecting the seed.

31. A method as claimed in claim 30 wherein the promoter is a hybrid promoter comprising an anther box from a CHS-A gene of *Petunia hybrida* fused to a CaMV 35S promoter.

32. A method as claimed in claim 27, wherein the promoter is a hybrid promoter comprising an anther box from a CHS-A gene of *Petunia hybrida* fused to a CaMV 35S promoter.

33. A method as claimed in claim 7, wherein the promoter is a hybrid promoter comprising an anther box from a CHS-A gene of *Petunia hybrida* fused to a CaMV 35S promoter.

* * * * *

SEQUENCE LISTING (1) GENERAL INFORMATION:

(iii) NUMBER OF SEQUENCES:   7

(2) INFORMATION FOR SEQ ID NO:1:

(i) SEQUENCE CHARACTERISTICS:
         (A) LENGTH:       16 base pairs
         (B) TYPE:         nucleic acid
         (C) STRANDEDNESS: double
         (D) TOPOLOGY:     linear (ii) MOLECULE TYPE:    DNA (genomic)

(iii) HYPOTHETICAL:  NO (iv) ANTI-SENSE:       NO (vi) ORIGINAL SOURCE:
         (A) ORGANISM:     Petunia hybrida (ix) FEATURE:
         (D) OTHER INFORMATION:    /label= EcoRI (xi) SEQUENCE DESCRIPTION: SEQ ID NO:1:

TNGAGGWGAM RDARWW                                                         16

(2) INFORMATION FOR SEQ ID NO:2:

(i) SEQUENCE CHARACTERISTICS:
         (A) LENGTH:       16 base pairs
         (B) TYPE:         nucleic acid
         (C) STRANDEDNESS: double
         (D) TOPOLOGY:     linear (ii) MOLECULE TYPE:    DNA (genomic)

(iii) HYPOTHETICAL:  YES (iv) ANTI-SENSE:       NO (vi) ORIGINAL SOURCE:
         (A) ORGANISM:     Petunia hybrida (xi) SEQUENCE DESCRIPTION: SEQ ID NO:2:

TAGAGGTGAC AGAAAT                                                         16

(2) INFORMATION FOR SEQ ID NO:3:

(i) SEQUENCE CHARACTERISTICS:
         (A) LENGTH:       16 base pairs
         (B) TYPE:         nucleic acid
         (C) STRANDEDNESS: double
         (D) TOPOLOGY:     linear (ii) MOLECULE TYPE:    DNA (genomic)

(iii) HYPOTHETICAL:  YES (iv) ANTI-SENSE:       NO (vi) ORIGINAL SOURCE:
         (A) ORGANISM:     Petunia hybrida (xi) SEQUENCE DESCRIPTION: SEQ ID NO:3:

TAGAGGTGACAAAAAT                                                          16

(2) INFORMATION FOR SEQ ID NO:4:

(i) SEQUENCE CHARACTERISTICS:

```
            (A) LENGTH:            16 base pairs
            (B) TYPE:              nucleic acid
            (C) STRANDEDNESS:      double
            (D) TOPOLOGY:          linear (ii) MOLECULE TYPE:          DNA (genomic)

(iii) HYPOTHETICAL:  YES (iv) ANTI-SENSE:             NO (vi) ORIGINAL SOURCE:
            (A) ORGANISM:          Petunia hybrida (xi) SEQUENCE DESCRIPTION: SEQ ID NO:4:

TNGAGGAGAA AAAGAT                                                           16

(2) INFORMATION FOR SEQ ID NO:5:

(i) SEQUENCE CHARACTERISTICS:
            (A) LENGTH:            16 base pairs
            (B) TYPE:              nucleic acid
            (C) STRANDEDNESS:      double
            (D) TOPOLOGY:          linear (ii) MOLECULE TYPE:          DNA (genomic)

(iii) HYPOTHETICAL:  YES (iv) ANTI-SENSE:             NO (vi) ORIGINAL SOURCE:
            (A) ORGANISM:          Petunia hybrida (xi) SEQUENCE DESCRIPTION: SEQ ID NO:5:

TAGAGGAGAA GTAATA                                                           16

(2) INFORMATION FOR SEQ ID NO:6:

(i) SEQUENCE CHARACTERISTICS:
            (A) LENGTH:            28 base pairs
            (B) TYPE:              nucleic acid
            (C) STRANDEDNESS:      double
            (D) TOPOLOGY:          linear (ii) MOLECULE TYPE:          DNA (genomic)

(iii) HYPOTHETICAL:  YES (iv) ANTI-SENSE:             NO (xi) SEQUENCE DESCRIPTION: SEQ ID NO:6:

GAGCTCTAGA GGTGACAGAA ATCTGCAG                                              28

(2) INFORMATION FOR SEQ ID NO:7:

(i) SEQUENCE CHARACTERISTICS:
            (A) LENGTH:            28 base pairs
            (B) TYPE:              nucleic acid
            (C) STRANDEDNESS:      double
            (D) TOPOLOGY:          linear (ii) MOLECULE TYPE:          DNA (genomic)

(iii) HYPOTHETICAL:  YES (iv) ANTI-SENSE:             NO (xi) SEQUENCE DESCRIPTION: SEQ ID NO:7:

GAGCTCTAGA GGTGACAGAA ATCTGCAG                                              28
```